(12) United States Patent
Schweisguth et al.

(10) Patent No.: US 8,015,026 B2
(45) Date of Patent: Sep. 6, 2011

(54) HEALTH MANAGEMENT SYSTEM FOR PEOPLE AND PETS

(75) Inventors: Diane Schweisguth, Lake Oswego, OR (US); Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 924 days.

(21) Appl. No.: 11/877,347

(22) Filed: Oct. 23, 2007
(Under 37 CFR 1.47)

(65) Prior Publication Data

US 2009/0106044 A1    Apr. 23, 2009

(51) Int. Cl.
*G06Q 10/00* (2006.01)
*G06Q 50/00* (2006.01)

(52) U.S. Cl. ................................. 705/2; 705/3

(58) Field of Classification Search .................. 119/720, 119/721; 340/400, 500; 702/160
See application file for complete search history.

(56) References Cited

U.S. PATENT DOCUMENTS

| | | | |
|---|---|---|---|
| 6,151,586 A | 11/2000 | Brown | |
| 7,280,097 B2 * | 10/2007 | Chen et al. | 345/156 |
| 7,409,924 B2 * | 8/2008 | Kates | 119/720 |
| 2005/0060344 A1 | 3/2005 | Pawlick | |
| 2005/0120978 A1 * | 6/2005 | Lalor | 119/721 |
| 2005/0177400 A1 * | 8/2005 | Rosenfeld et al. | 705/3 |
| 2005/0209887 A1 | 9/2005 | Pollner | |
| 2005/0250440 A1 * | 11/2005 | Zhou et al. | 455/12.1 |
| 2006/0129432 A1 | 6/2006 | Choi et al. | |
| 2006/0183980 A1 | 8/2006 | Yang | |
| 2007/0204804 A1 * | 9/2007 | Swanson et al. | 119/721 |
| 2008/0143516 A1 * | 6/2008 | Mock et al. | 340/539.14 |
| 2008/0272920 A1 * | 11/2008 | Brown | 340/573.3 |

FOREIGN PATENT DOCUMENTS

| WO | WO-2005083621 | 9/2005 |
|---|---|---|
| WO | WO-2006109954 | 10/2006 |

* cited by examiner

*Primary Examiner* — Gerald J. O'Connor
*Assistant Examiner* — Linh-Giang Michelle Le
(74) *Attorney, Agent, or Firm* — Suiter Swantz pc llo (57) ABSTRACT

A system, apparatus and method for simultaneously managing health of different individuals and pets over a network are provided. The present invention provides a strategy to motivate an individual to exercise. In one embodiment of the invention, the pet is being used as a means of monitoring the pet-owner's compliance with the exercise regimen. A healthcare provider is provided for transmitting health and physical exercise related scripted content into communication devices of the individuals and the pets. Data related to physical activities of the pets and the individuals are collected and are sent to the remote server. The healthcare provider linked with the remote server is accessed by physicians and the veterinarians for analyzing the data related to the physical activities and providing feedback messages accordingly.

25 Claims, 11 Drawing Sheets

Sammy's Activity Record: 10/02/06

| 7am | Walk message sent |
|---|---|
| 7am | Walk message received |
| 7:30am | Took Sammy for 20 minute walk |
| 1pm | Walk message sent; no response |
| 1:30 | Walk message sent; no response |
| 2:00pm | Walk message sent |
| 2:00pm | Walk message received |
| 2:10pm | Played catch for 5 minutes |

Sammy's Medication Report: 10/02/06

| 7am | Med reminder message sent |
|---|---|
| 7am | Med reminder message received |
| 7:10am | enalpril 5mg given |
| 7pm | Med reminder message sent |
| 7pm | Med reminder message received |
| 7:15pm | enalpril 5mg given |
| 7:20pm | Refill reminder sent |

Figure 7

HEALTH MANAGEMENT SYSTEM FOR PEOPLE AND PETS

BACKGROUND

A. Technical Field

The present invention relates generally to health management and, more particularly to, a health management system that integrates a pet's health management program with an owner's health management program.

B. Background of the Invention

The importance of health management in today's society is well understood. An increasing number of healthcare providers are commencing healthcare programs these days. A healthcare program may include a particular diet, exercise, rest and monitoring of health-related indicators such as weight, blood pressure, peak flow and the like. Presently, people are also concerned with their pet's health and want proper health management for their pets. Hence, a number of health programs are also being initiated for pets. Obesity is a serious health factor for people and pets. An obesity condition is generally treated by means of regular physical exercise. However, if a physical exercise regimen is not correctly followed, then the beneficial effects of physical exercise may be negated.

Monitoring of a healthcare program for individuals now includes remote management provided by web-based technology. People are now able to attend health management programs at their respective locations. Typically, in a web-based health program, input parameters are gathered from subscribed people through various sensors and activity meters at the subscriber's end, and health related messages are provided to the subscriber based on the measured input parameters. The subscriber then follows the steps suggested in the message and performs the exercises accordingly. However, such attempts to solve the problem of remotely monitoring physical activities of a person fails to properly measure and monitor the physical activities of pets. A healthcare program for an obese pet may include engaging the pet with physical activities. The ability to remotely measure and monitor physical activity of a pet is limited. Additionally, no health management system exists that remotely monitors and manages physical activity of people and pets simultaneously.

Thus, there is a need for a new and improved health management system that integrates a pet's health management program with the owner's health management program.

SUMMARY OF THE INVENTION

The present invention provides a system, apparatus and method for integrating a pet's health management program with the owner's health management program. In one embodiment of the invention, a health management system for remotely monitoring the activities of at least one pet and at least one person is provided. A health management system of the present invention may comprise a remote server capable of receiving messages from at least one remote healthcare provider, a user communication device and a pet device.

A pet device, such as a pet-collar or tag, may be configured to measure physical activities of the pet and send information on physical activities of the pet to an interactive user communication device such as a PDA, a personal computer or a mobile phone. The user communication device may be configured to receive said messages from the remote server, and receive said measurements of physical activities of the pet from the pet device. This information on physical activities of the pet may be then delivered to the remote server by said user communication device.

A remote healthcare provider, such as a computer associated with a medical doctor or veterinarian, is configured to communicate with the remote server for accessing the information on physical activities of the pet and to transmit messages to go to the interactive user communication device. The interactive user communication device also records various health-related parameters of the person, wherein one of the health-related parameters of the person is physical activity and the physical activity of the person is derived from the measurement of the physical activities of the pet.

According to the present invention, separate databases may be maintained for storing information on physical activities of the pet and the person, which may be accessed by veterinarians and physicians respectively.

In one embodiment of the invention, a method for remotely monitoring the activities of at least one pet and at least one person within a health management system is provided wherein messages from at least one remote healthcare provider are transmitted to a remote server. A pet device is configured for measuring physical activities of the pet, and sending information on physical activities of the pet to an interactive user communication device. Said interactive user communication device is configured for receiving messages from the remote server and measuring physical activities of the pet-owner and sending information on physical activities of the pet to the remote server. The healthcare provider is also configured to communicate with the remote server for accessing the information on physical activities of the pet and transmitting messages to go to the interactive user communication device.

In one embodiment of the present invention a pet device is provided for measuring physical activities of the pet and sending information on physical activities of the pet to an interactive user communication device. The pet device comprises an accelerometer for detecting the physical activities of a pet; a leash sensor for detecting the proximity of the pet owner to the pet; a microprocessor configured to process the output-data of accelerometer and output-data of leash sensor; a radio frequency transmitter configured to transmit said processed output-data to a remote server; detecting means to detect the messages being received on an interactive user communication device; and indicators for indicating the detection of said messages.

Other objects, features and advantages of the invention will be apparent from the drawings, and from the detailed description that follows below.

BRIEF DESCRIPTION OF THE DRAWINGS

Reference will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

A system, apparatus and method for simultaneously managing health of different individuals and pets over a network are provided. In one embodiment of the invention, a pet may be used as a means of monitoring the pet-owner's compliance with the exercise regimen. Health and physical exercise related scripted content are transmitted into communication devices of individuals in order to remotely train and monitor each individual and his pet. The transmitted script is based on the data collected at the individual's end. Said data is basically the measurement of physical activities of the individuals and pets and is sent to a remote server. The data sent to the remote server is accessed by physicians and veterinarians for analysis and preparation of the script to be transmitted to the communication devices of the individuals.

The following description is set forth for purpose of explanation in order to provide an understanding of the invention. However, it is apparent that one skilled in the art will recognize that embodiments of the present invention, some of which are described below, may be incorporated into a number of different computing systems and devices. The embodiments of the present invention may be present in hardware, software or firmware. Structures shown below in the diagram are illustrative of exemplary embodiments of the invention and are meant to avoid obscuring the invention. Furthermore, connections between components within the figures are not intended to be limited to direct connections. Rather, data between these components may be modified, reformatted or otherwise changed by intermediary components.

Reference in the specification to "one embodiment", "in one embodiment" or "an embodiment" etc. means that a particular feature, structure, characteristic, or function described in connection with the embodiment is included in at least one embodiment of the invention. The appearances of the phrase "in one embodiment" in various places in the specification are not necessarily all referring to the same embodiment.

A. Overview—

Figure 1:
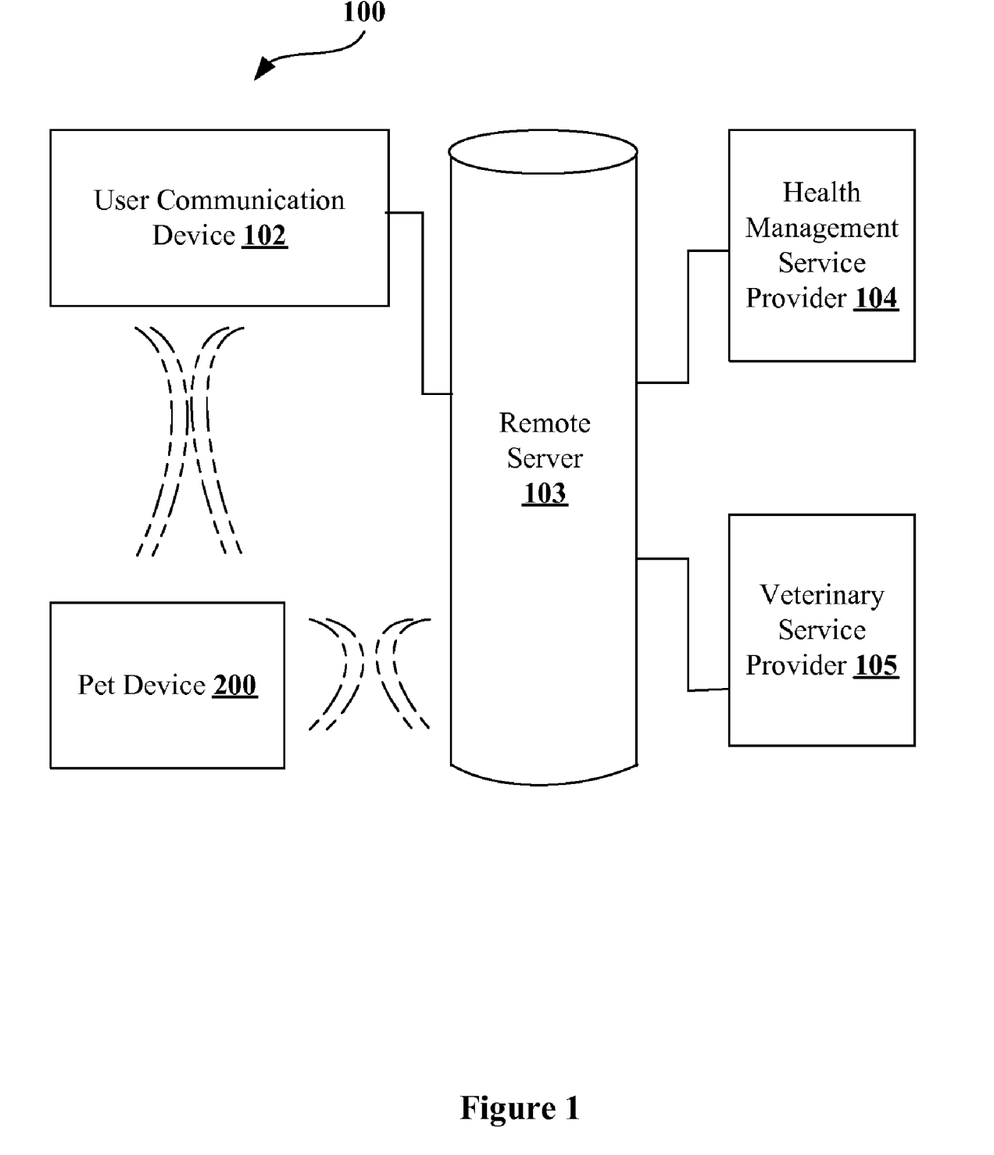
FIG. 1 is a block diagram illustrating a health management system according to one embodiment of the invention.

FIG. 1 depicts a block diagram illustrating a health management system 100 according to one embodiment of the invention. Said system 100 comprises at least one pet device 200 that is configured to measure physical activities of the pet and send information on physical activities of the pet to an interactive communication device 102. The pet device 200 may include a microprocessor to process the data relating to the measured physical activity of the pet.

The interactive user communication device 102 may be communicatively coupled to a remote server 103. Said user communication device 102 receives the information on physical activities of the pet from a pet device and transmits the same to the remote server 103 over a communication network.

The server 103 is preferably a World Wide Web server and the communication network is preferably the Internet. Alternatively, the server 103 may also comprise a single stand-alone computer or multiple computers distributed throughout a network. The user communication device 102 is preferably a personal computer, remote terminal, a mobile phone, a personal digital assistant, or web TV unit connected to the server 103 via the Internet. The user communication device 102 functions as a remote interface for entering in the server 103 messages and queries to be communicated to the pet owners.

The pet device of the health management system 100 is suitable for measuring pet activities and sensing the activities of the pet owner when he/she is in close proximity with the pet. The remote server 103 may be coupled to a health provider that may be configured to communicate with the remote server 103 for accessing the information on physical activities of the pet and to transmit messages or scripts to go to the interactive user communication device 102. The interactive user communication device also records various health-related parameters of the person such as physical activity. It is contemplated that the physical activity of the person may be derived from the measurement of the physical activities of the pet.

The user communication device 102 stores a software application that allows the users to receive and send communications from and to health care providers (veterinarians and physicians). The communications may include, but are not limited to health care messages and reminders, physical activity records, other messages.

The pet device 200 may be incorporated within a pet collar or tag that detects (e.g. through Bluetooth technology) when a communication from a health care provider has been received on the pet owners device 102. The communications that are being received on the interactive user communication device 102 may be detected by the detecting means such as a Bluetooth detector provided on the pet device 200. Thereafter the pet device 200 alerts the owner regarding a communication from a healthcare provider by an indicator such as a visual clue such as a LED light and/or an audio clue, such as a beep or music. As mentioned earlier, the user interactive communication device 102 and the pet device 200 are configured to communicate with each other. For example, the pet's communication device 200 (visual or audio clue) turns off when the pet owner activates his or her communication device 102 to receive the message.

The remote server 103 maintains a first database for storing information on various physical activities of the pet, and a second database for storing information on various physical activities of the pet owner. The health care providers 104, 105 access these databases for providing health related messages and tasks from the pet device to the owner communication device 102.

For instance, a veterinarian 105 may schedule messages to go to the owner from the pet device. These messages may be exercise/activity reminders, medication reminders, steps involved in treatment regimens, etc as mentioned earlier. When the message is sent, the pet device signals that a message is waiting on the user communication device 102. The owner responds to the message via the user communication device 102 and does the task and records the activity on the user communication device 102.

This information on completion of the task is sent to the remote server 103, where it can be accessed by the veterinarians 105, and, if the owner is subscribed to Health Care Provider 104, then the owner's health care provider 104 can also schedule messages or tasks to go to the owner from the pet, and receive data from the owner regarding the message or task.

The health care providers 104, 105 of both the pet and the owner use the data captured as a decision support tool for health care management.

B. Pet Device

Figure 2:
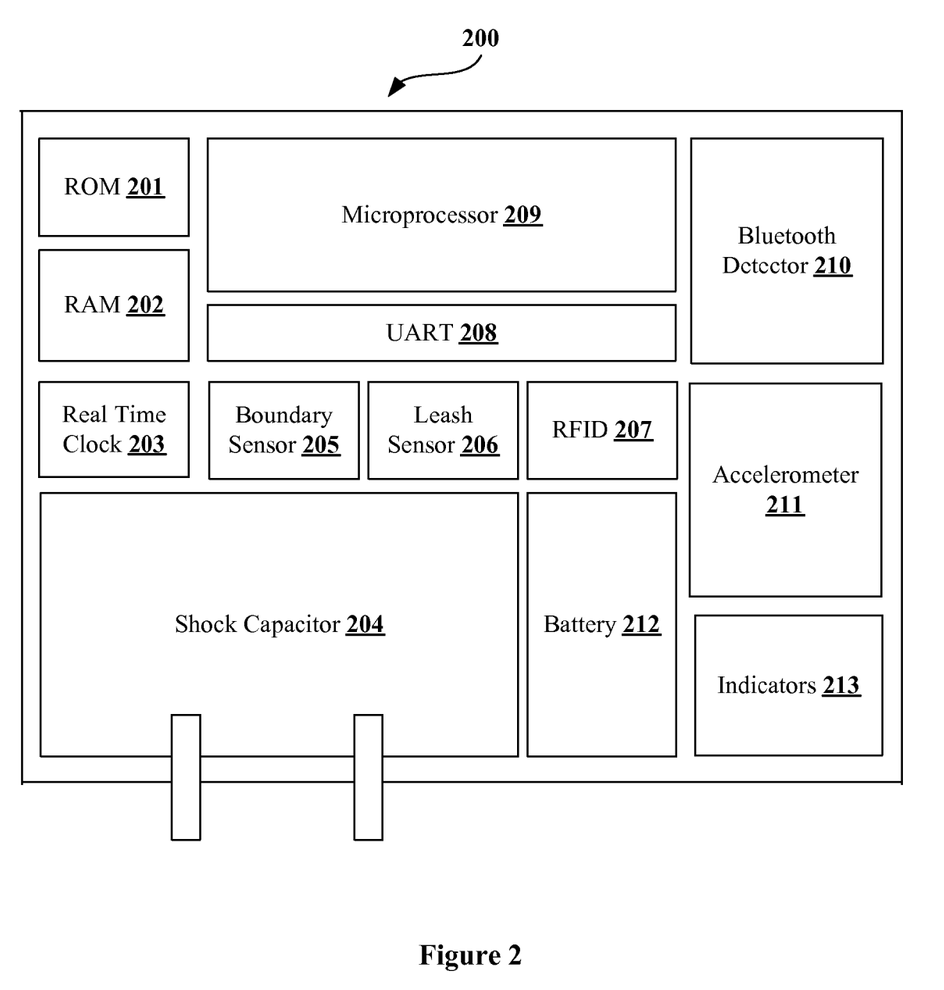
FIG. 2 is a block diagram of the pet device according to one embodiment of the invention.

FIG. 2 shows a block diagram of pet device 200 according to one embodiment of the invention. The pet device 200 measures physical activities of the pet and sends information on physical activities of the pet to the interactive user communication device. As shown in the figure, the pet device 200 comprises a microprocessor 209, which controls processing of various data within the apparatus as well as transmission of measured data. A read only memory ROM 201 is provided to store various instructions and software codes which are required by the microprocessor 209 during its operation.

A random access memory RAM 202 is provided to store various data and information that are to be used by the microprocessor 209. Synchronization of data transmission within the apparatus may be guided by a real time clock 203. The real time clock may also provide reference signals in transmission of data from the pet device 200. A transmitter, preferably the Universal Asynchronous Receiver Transmitter (UART) 208 is provided in the pet device for parallel-to-serial conversion of digital data to be transmitted and the serial-to-parallel conversion of digital data that has been transmitted.

The detection of physical activity of the pet and the pet owner (during proximity) may be accomplished by an accelerometer 211, which detects physical movement of the pet and the pet owner (when the pet owner is in close proximity to the pet or carrying the pet device as an activity tracker device).

As shown in FIG. 2, a radio frequency receiver (RF receiver RFID) 207 is provided to receive RF signals from various RFID tags that may be incorporated within owner's leash or owner's communication device. Thus, when the owner is in close proximity to the pet, the RFID 207 detects the owner's proximity. Further, owner's leash may also incorporate a proximity sensor capable of sensing the pet's proximity. Hence a leash sensor 208 is provided as a complementary to said proximity sensor for detecting the proximity of the pet owner to the pet. 205. Thus, a correlation between activities of the pet and the owner is always obtained when both are in close proximity to each other. The messages being received on an interactive user communication device are detected by the detecting means such as Bluetooth detector 210 provided on the pet device 200. The indications of the received messages are provided by the indicators 213. Indicators 213 could also be used as signals for the visually or hearing impaired owners, and signals for pet training, etc.

A rechargeable battery 212 is also provided for supplying power to the pet device 200. In addition, the pet device also has a boundary sensor 207 and a shock capacitor 204, so that when the pet goes beyond a predefined boundary, the pet may be given a mild shock and can be tracked.

Alternatively, the accelerometer 211 or the pet activity meter embedded within the pet device 200 or within an ancillary activity product such as a ball or bone that would track the pet's activity level. Further, the pet owner activity meter 211 may also be embedded within the pet owner's device, or a pet owner's lease or wristband that would track the pet owner's activity. A method to correlate these activities may also be provided within the pet device 200.

C. Working of Health Management System

Figure 3:
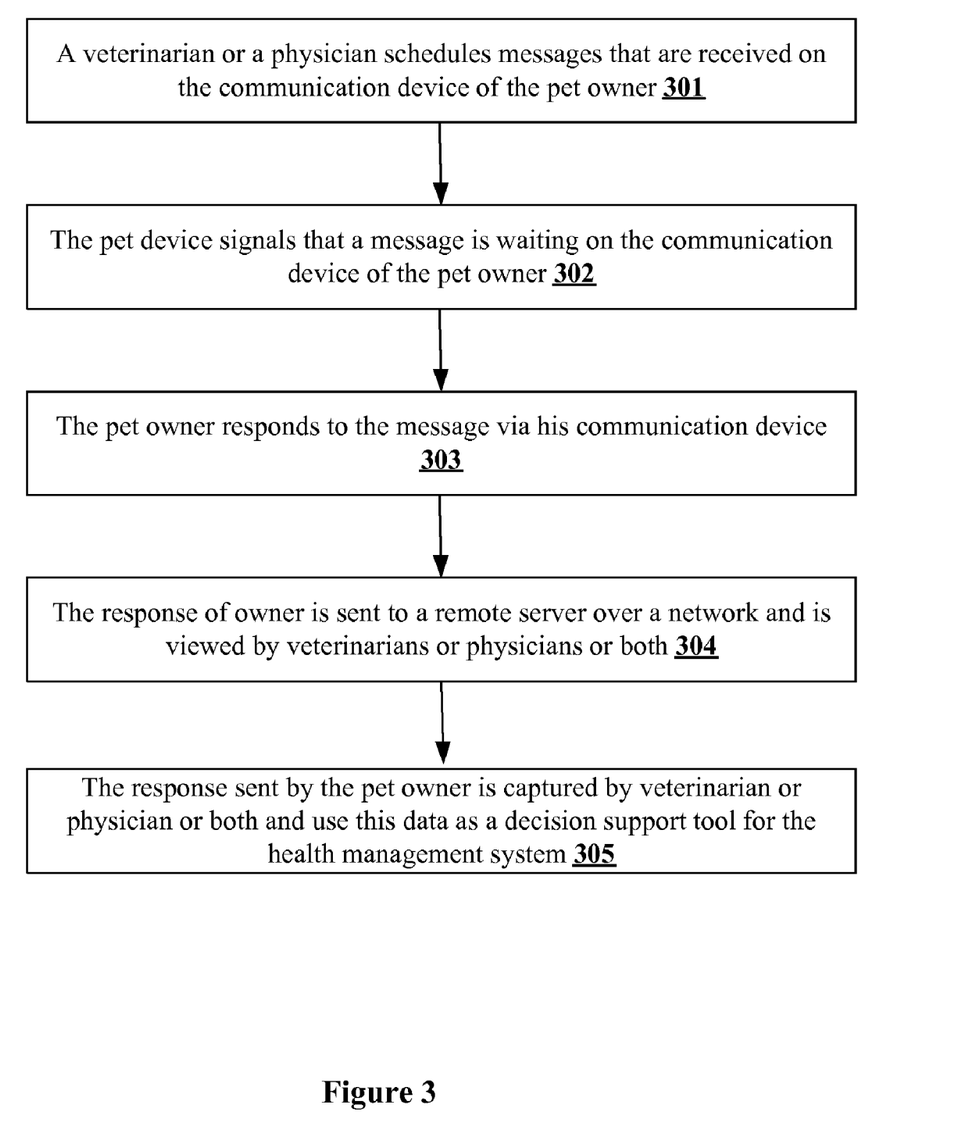
FIG. 3 is a flowchart describing the working of the health management system according to one embodiment of the invention.

FIG. 3 is a flowchart describing the working of the health management system. According to one embodiment of the invention, one or more remote health care application is communicatively coupled to a remote server in order to provide health related messages and scripts to their subscribers over a network. These remote health care applications are accessed by healthcare providers who generate health related messages or scripts. These healthcare providers may be veterinarians or physicians as explained previously.

Referring to FIG. 3, in step 301, the veterinarian or the physician or both schedule messages to go to the owner from the pet device through the remote server. These messages may be exercise/activity reminders, medication reminders, steps involved in treatment regimens, etc.

Figure 4A:
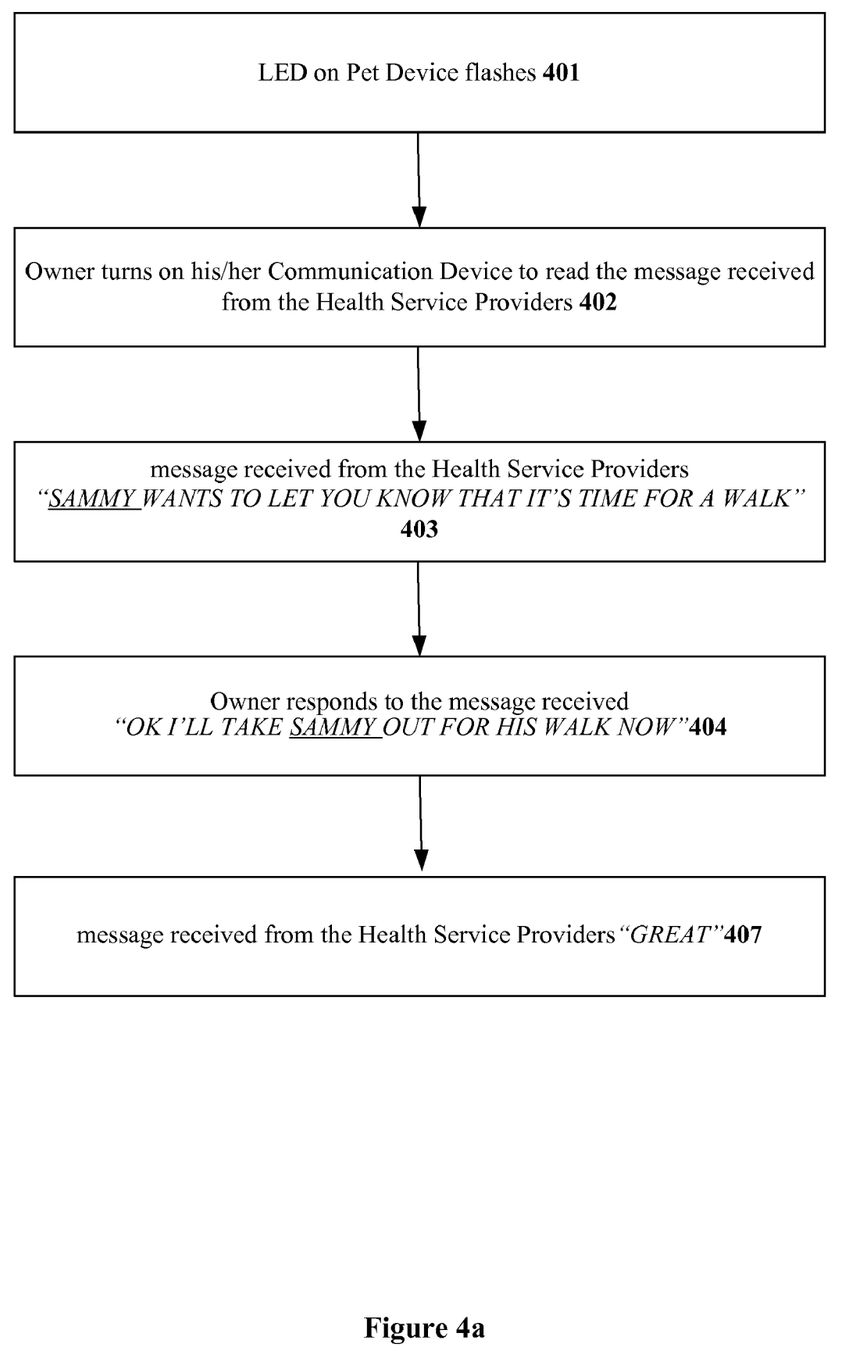
FIG. 4a is an example of health and physical exercise related communication between the health service providers and the end users according to one embodiment of the invention.
Figure 4B:
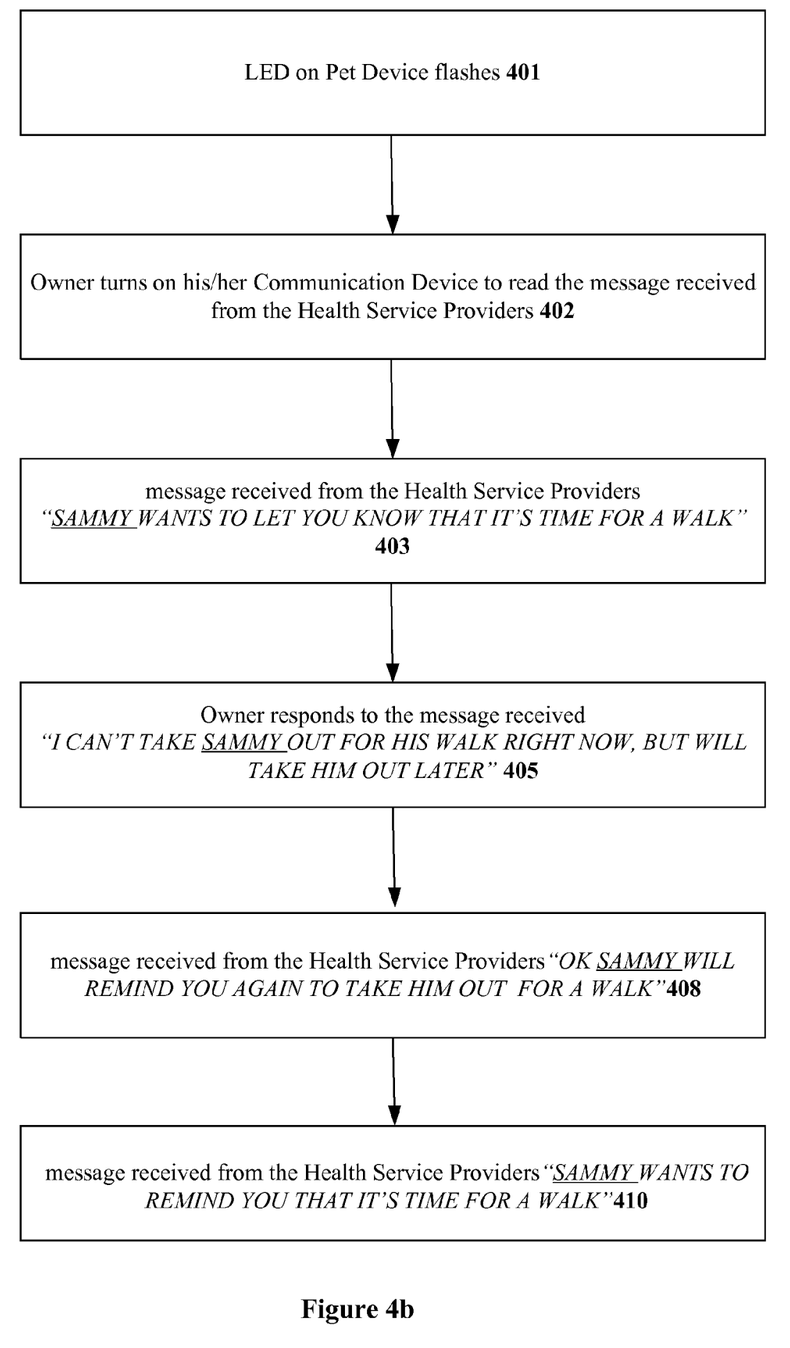
FIG. 4b is an example of health and physical exercise related reminder messages that may be sent from the health service providers to the end users according to one embodiment of the invention.
Figure 4C:
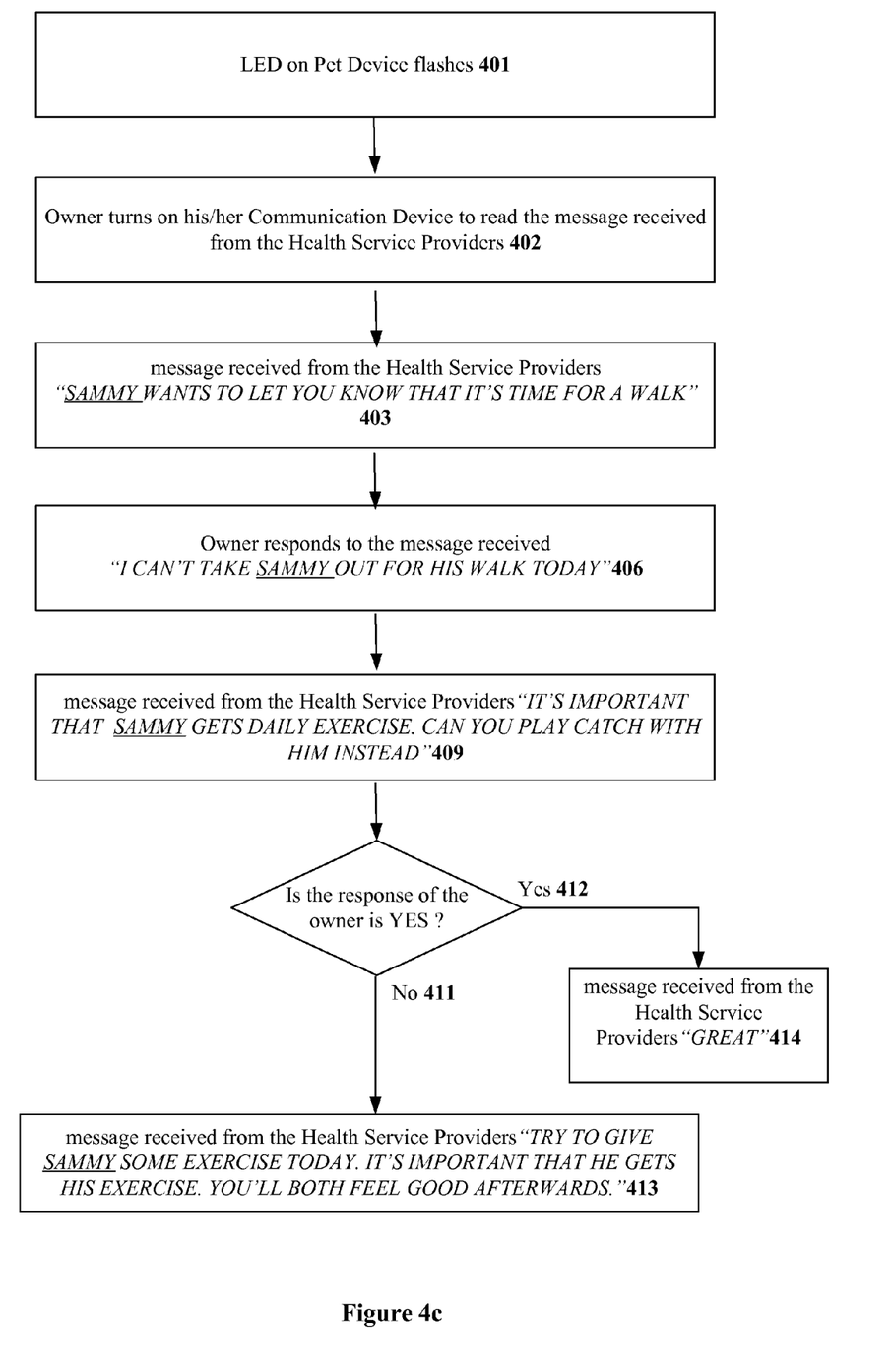
FIG. 4c illustrates how the end user may be motivated to perform physical exercises along with his/her pet according to one embodiment of the invention.

In step 302 the pet device signals that a message is waiting on the communication device of the pet owner. In step 303, the pet owner responds to the message via his/her communication device. The pet owner completes the task according to the received message and records the activity on the communication device. In step 304, this response is sent to the remote server, where it can be accessed by the veterinarian, and, the physician. Thus the veterinarians and the physician receive data from the pet and the pet owner regarding the message or task. In step 305 the health care providers of both the pet and the pet owner use the data captured as a decision support tool for the health care management system. FIG. 4a, FIG. 4b and FIG. 4c illustrate the flow of health and physical exercise related scripted content between the health service providers and the end users. As soon as a message is sent from the health care provider 105 (of FIG. 1), the pet device 102 (of FIG. 1) gives indication to the owner or the end user about the message received on his/her communication device 102 (of FIG. 1) 401. Subsequently, the end user or the owner of the pet may turn on this/her communication device to read the received message 402.

On receipt of the health related messages, the owner may respond and perform certain activities based on the messages received. The responses and the activities of the owner form inputs for the health care providers and based on these inputs, the health service providers may send subsequent scripts or health related scripted content to the communication device of the owner.

For instance, as shown in FIG. 4a, one of the health-related scripts or messages displayed on the user communication device 102 (of FIG. 1) may be read as "SAMMY WANTS TO LET YOU KNOW THAT ITS TIME FOR A WALK" 403 where 'SAMMY' may be the name of the pet. On receipt of this message 403, the owner may send a response message saying "OK I'LL TAKE SAMMY OUT FOR HIS WALK NOW" 404 and receive a message "GREAT" 407 from the health care provider 105 (of FIG. 1). The pet device 200 (of FIG. 1) may then gather data during the 'WALK' of the pet and the owner, and this data may be sent to the remote server 103 (of FIG. 1).

Similarly, as shown in FIG. 4b, when the user communication device 102 (of FIG. 1) receives the message "SAMMY WANTS TO LET YOU KNOW THAT ITS TIME FOR A WALK" 403, the owner may respond to the message 403 by saying "I CAN'T TAKE SAMMY OUT FOR HIS WALK RIGHT NOW, BUT WILL TAKE HIM OUT LATER" 405 and thus receive a message from the health care provider 105 (of FIG. 1) as "OK SAMMY WILL REMIND YOU AGAIN TO TAKE HIM OUT FOR A WALK" 408. Consequently, several reminders 410 saying SAMMY WANTS TO REMIND YOU THAT ITS TIME FOR A WALK" may be send to the owner from the health care providers 105 (of FIG. 1) in case no data is recorded regarding the activity after certain interval of time.

Further, as shown in FIG. 4c, when the user communication device 102 (of FIG. 1) receives the message "SAMMY WANTS TO LET YOU KNOW THAT ITS TIME FOR A WALK" 403, the owner may also respond to the message by saying "I CAN'T TAKE SAMMY OUT FOR HIS WALK TODAY" 406. The health service providers 105 (of FIG. 1) may then suggest the owner about other physical activities (e.g. "PLAY CATCH" 409) as alternates of the 'WALK' activity. The owner may or may not agree to perform the alternative activities as suggested by the health service providers 105 (of FIG. 1). On agreeing 412 to the suggested activity, the owner may receive a message on the user communication device 102 (of FIG. 1) "GREAT" 414 from the health care provider 105 (of FIG. 1). While performing the activity by the owner along with his/her pet, the pet device 200 (of FIG. 1) measures the activities of the pet and the owner and the data related to such activities is sent to the remote server. 103 (of FIG. 1).

If the owner responds negatively 411 to the alternative suggestion 409 of the health care provider 105 (of FIG. 1), another message saying "TRY TO GIVE SAMMY SOME EXERCISE TODAY. IT'S IMPORTANT THAT HE GETS HIS EXERCISE. YOU'LL BOTH FEEL GOOD AFTERWARDS."413 may be flashed on the user communication device 102 (of FIG. 1) describing the importance of physical activities and so on.

Figure 5A:
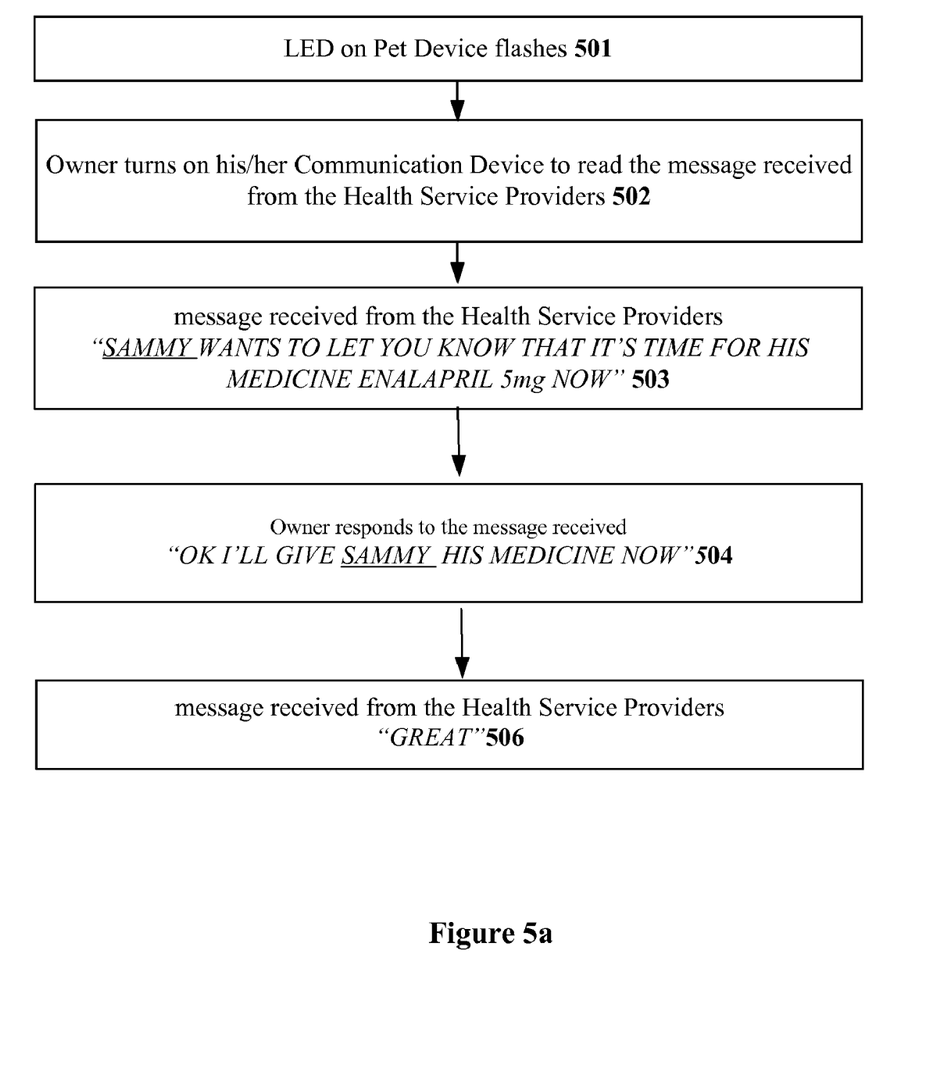
FIG. 5a illustrates pet's treatment and medication related communication between the health service providers and the end users according to one embodiment of the invention.
Figure 5B:
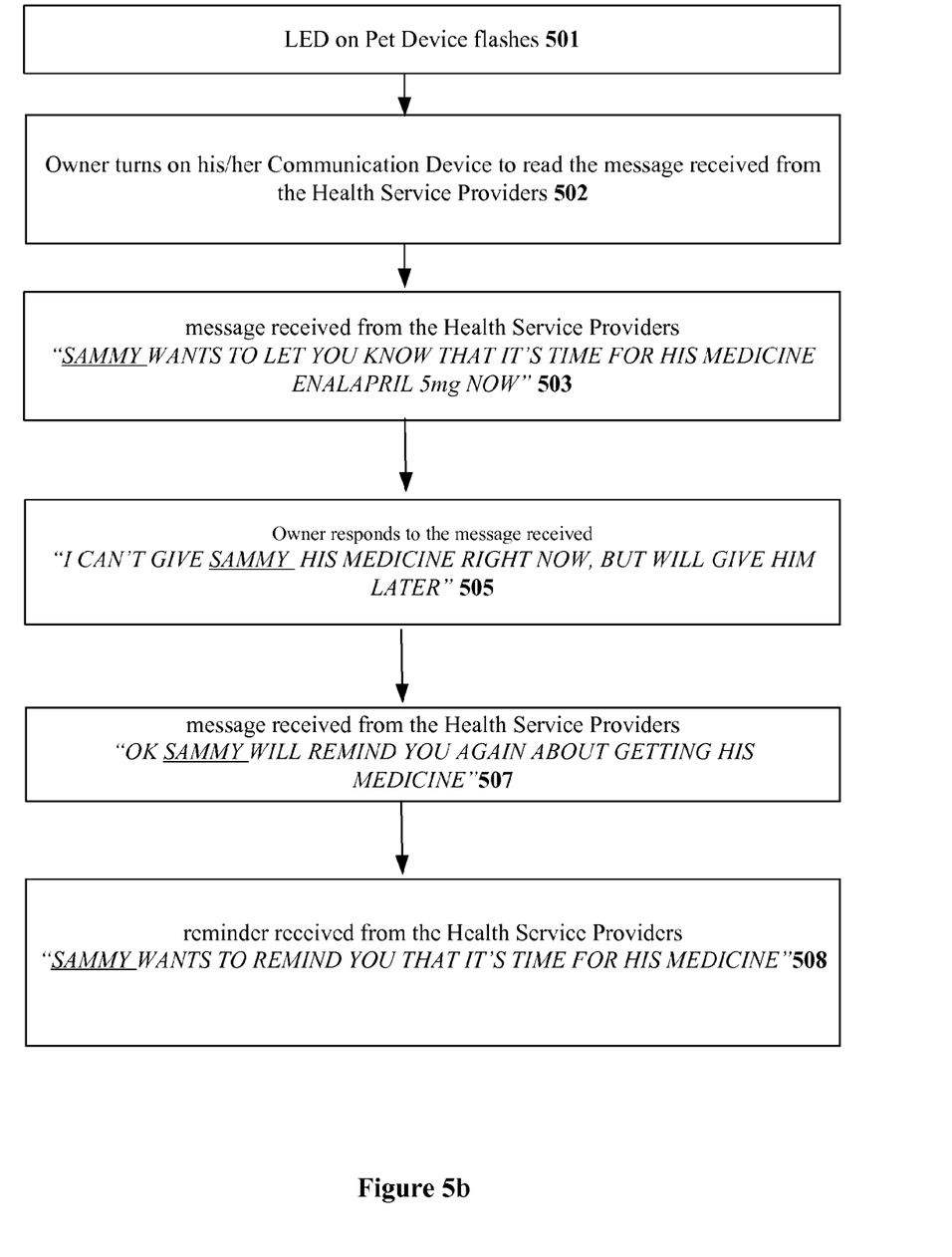
FIG. 5b is an example of pet's treatment and medication related reminder messages that may be sent from the health service providers to the end users according to one embodiment of the invention.
Figure 5C:
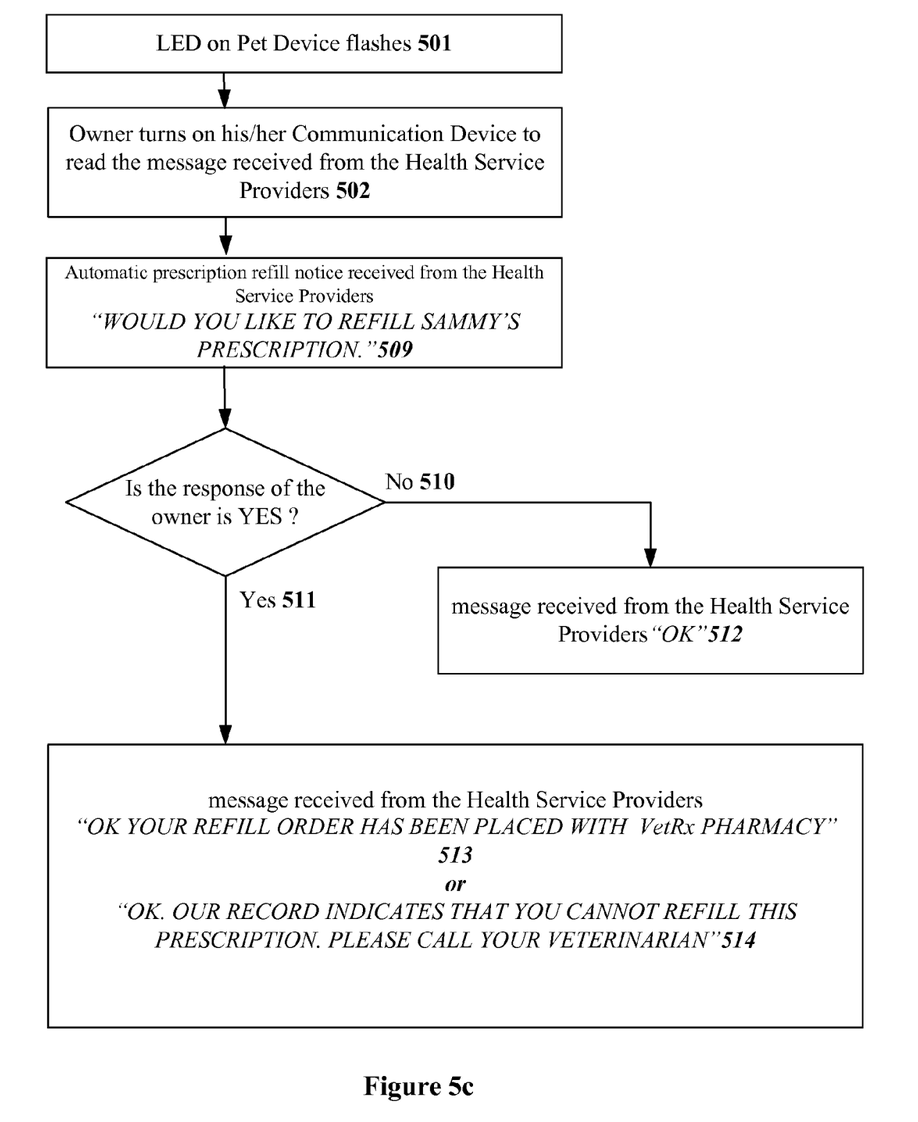
FIG. 5c illustrate sending an automatic prescription refill notice sent from the health service providers to the end users according to one embodiment of the invention.

FIG. 5a, FIG. 5b and FIG. 5c illustrate the flow of pet treatment and medication related scripted content between the health service providers 105 (of FIG. 1) and the end users. When a message is sent from the health care provider 105 (of FIG. 1), the LED on the pet device 102 (of FIG. 1) flashes to give an indication to the owner 501. The end user or the owner of the pet may turn on this/her communication device 102 (of FIG. 1) to read the received message 502.

As shown in FIG. 5a, one of the message may be read as "SAMMY WANTS TO LET YOU KNOW THAT ITS TIME FOR HIS MEDICINE ENALAPRIL 5 mg" 503. On receipt of this message 503, the owner may send a response message saying "OK I'LL GIVE SAMMY HIS MEDICINE NOW" 504 and receive a message "GREAT" 506 from the health care provider 105 (of FIG. 1).

Similarly, as shown in FIG. 5b, the owner may respond to the message 503 by sending a message "I CAN'T GIVE SAMMY HIS MEDICINE RIGHT NOW, BUT WILL GIVE HIM LATER" 505 and thus receive a message "OK SAMMY WILL REMIND YOU AGAIN ABOUT GETTING HIS MEDICINE" 507. Consequently, several reminder messages such as "SAMMY WANTS TO REMIND YOU THAT IT'S TIME FOR HIS MEDICINE" 508 may be send to the owner from the health care providers 105 (of FIG. 1) in case no data is recorded in the pet device 200 (of FIG. 1) and subsequently in the remote server 103 (of FIG. 1) regarding the medicine after certain interval of time.

As shown in FIG. 5c, the owner may also receive an automatic prescription refill notice saying, "WOULD YOU LIKE TO REFILL SAMMY'S PRESCRIPTION" 509. On agreeing to refill prescription 511, the owner may receive a message "OK YOUR REFILL ORDER HAS BEEN PLACED WITH VetRx PHARMACY" 513 or "OK OUR CASE RECORD INDICATES THAT YOU CANNOT REFILL THIS PRESCRIPTION. PLEASE CALL YOUR VETERINARIAN" 514 from the health care provider 105 (of FIG. 1). The owner may also respond negatively 510 to Sammy's prescription refill notice and receive an acknowledgement such as "OK" 512 from the health care provider for 105 (of FIG. 1) his/her response.

Thus the owner is able to record the activity or medication administration in his/her communication device 102 (of FIG. 1) such as PDA along with any notes, etc.

Figure 6:
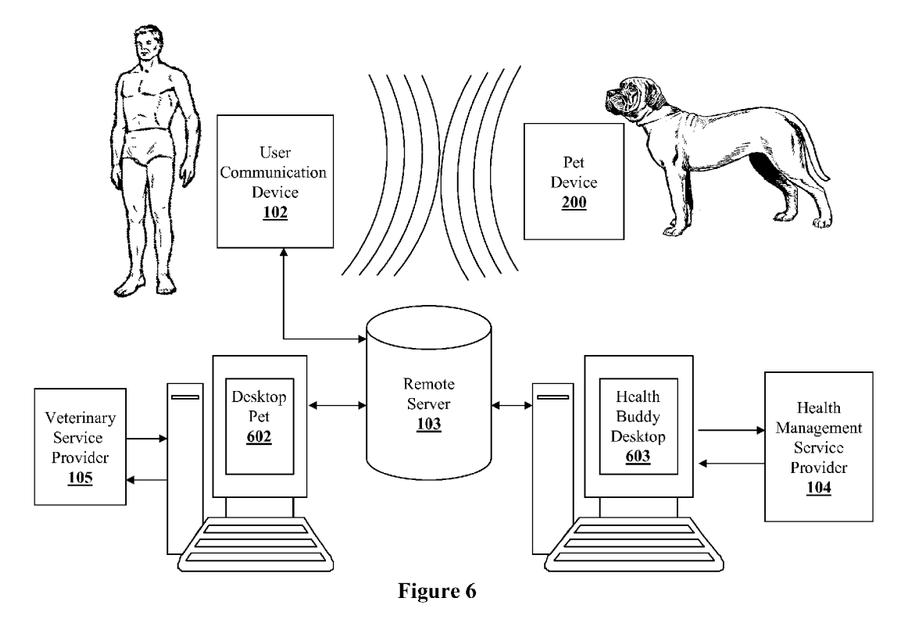
FIG. 6 illustrates the application of Health Buddy® Desktop within the health management system according to one embodiment of the invention.

FIG. 6 illustrates the application of Health Buddy® Desktop within the health management system according to one embodiment of the invention. As explained earlier, the data recorded on the pet device 200 pet device may be sent to the user communication device 102 using wireless technology such as Bluetooth. The recorded data contain information on physical activities of the pet 604. The data sent to the user communication device 102 may be captured or downloaded into the remote server 103 where a veterinary service provider 105 may retrieve it using the Pet Desktop 602. The pet desktop 602 may be a computer system used by the pet owner. The pet desktop 602 may be linked to the remote server 103 for communication.

The remote server 103 may also be accessed by the health management service provider 104 for retrieving the data captured or downloaded from the user communication device 102 into the remote server 103 through an interface, such as the Health Buddy® Desktop 603. The Health Buddy® Desktop refers to the 'Health Buddy® System' of Health Hero Network that serves as an interface between patients at home and care providers, facilitating patient education and monitoring of chronic conditions. The 'Health Buddy® System' includes monitoring technologies, clinical information databases, Internet-enabled decision support tools, health management programs and content development tools. According to another embodiment of the invention, if the owner is using a Direct to Consumer version, he or she could also be able to download or print out the information/record.

Figure 7:
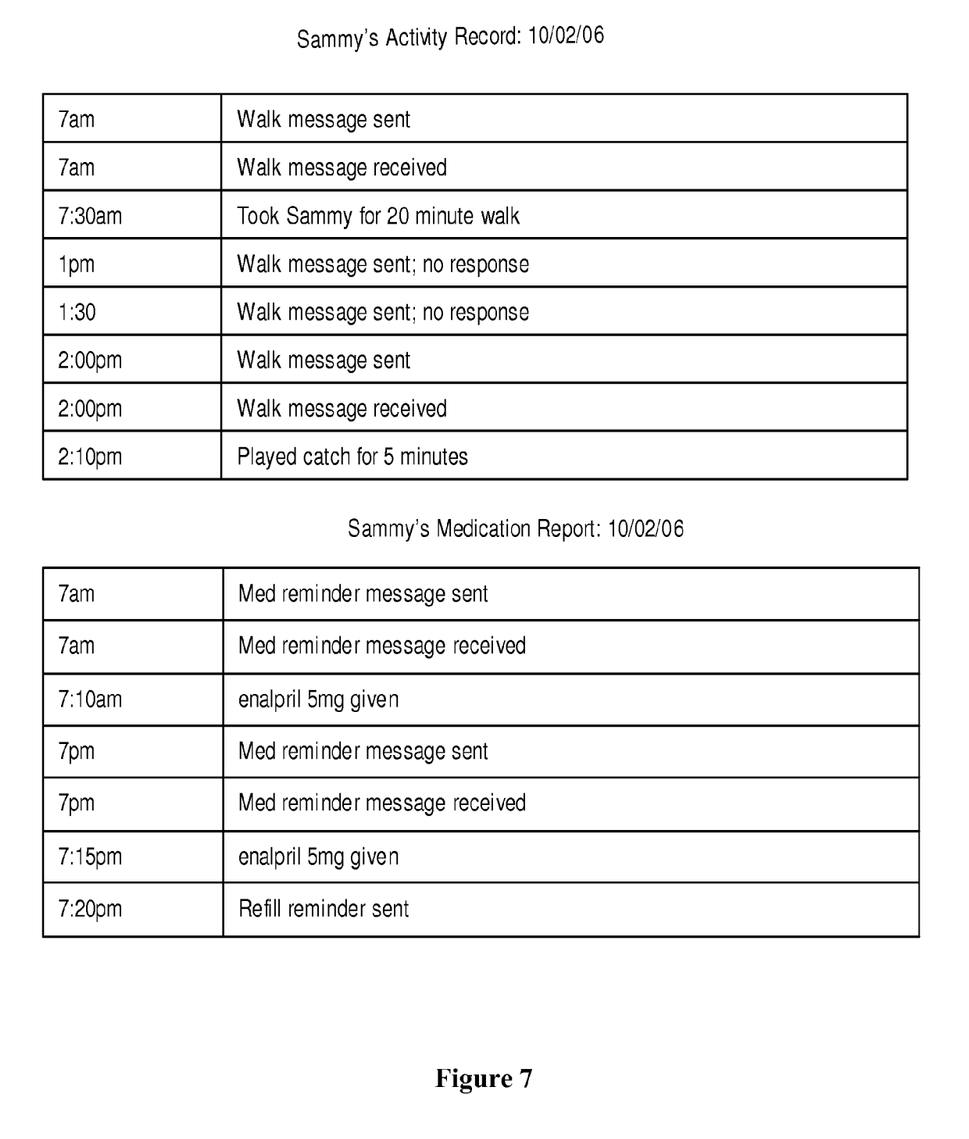
FIG. 7 shows sample reports for veterinarians according to one embodiment of the invention.

FIG. 7 shows sample reports for veterinarian. The reports include the physical activity and medication report of a pet (Sammy) that may be referred by the veterinarian. The veterinarian may use these reports as a decision support tool for the health care management.

Thus, a network-based system is provided that motivates a pet owner with chronic conditions to maintain a pet-assisted health improvement regimen, (and if indicated—vise versa—that the pet owner would assist the pet with a chronic condition to maintain the pet's health.) Further it is also possible to send data to the veterinary practice to monitor and improve the health of the pet. Chronic care management, medication therapy, monitoring and management programs for animals are also possible.

The foregoing description of the invention has been described for purposes of clarity and understanding. It is not intended to limit the invention to the precise form disclosed. Various modifications may be possible within the scope and equivalence of the appended claims.

What is claimed is:

1. A health management system for remotely monitoring the activities of at least one pet and at least one person, the health management system comprising:

a remote server;
at least one remote healthcare provider computer for transmitting messages to the remote server;
a pet device configured to:
  measure physical activities of the pet, and send information on physical activities of the pet to an interactive communication device; and
an interactive user communication device for communicating with the person and configured to:
  receive said messages from said remote server, and
  receive said measurements of physical activities of the pet from the pet device and send information on physical activities of the pet to the remote server;
wherein, the remote server is configured to access the information on physical activities of the pet and to transmit messages to go to the interactive user communication device, the interactive user communication device records various health-related parameters of the persons where one of the health-related parameters of the person is physical activity and the physical activity of the person is derived from measurement of the physical activities of the pet.

2. The health management system of claim 1, wherein said remote server maintains a first database for storing information on various physical activities of the pet.

3. The health management system of claim 1, wherein said remote server maintains a second database for storing information on various physical activities of the pet owner.

4. The health management system of claim 1, wherein said pet device is formed within a pet collar.

5. The health management system of claim 1, wherein said interactive user communication device is a personal digital assistant (PDA) device.

6. The health management system of claim 1, wherein said interactive user communication device is a personal computer.

7. The health management system of claim 1, wherein said interactive user communication device is a mobile phone.

8. The health management system of claim 1, wherein said pet device detects the messages that are being received on the interactive user communication device through Bluetooth technology.

9. The health management system of claim 1, wherein said messages include medication and treatment reminders, for the pet and the pet owner.

10. The health management system of claim 1, wherein the remote health care provider is a physician.

11. The health management system of claim 1, wherein the remote health care provider is a veterinarian.

12. A health management system for remotely monitoring the activities of at least one pet and at least one person, the health management system comprising:
a remote server;
at least one remote healthcare provider computer for transmitting messages to the remote server;
a pet device configured to:
  measure physical activities of the pet, and send information on physical activities of the pet to an interactive communication device; and
an interactive user communication device for communicating with the person and configured to:
  receive said messages from said remote server, and
  receive said measurements of physical activities of the pet from the pet device and send information on physical activities of the pet to the remote server;
  wherein, the remote server is configured to access the information on physical activities of the pet and to transmit messages to go to the interactive user communication device, wherein said pet device comprises a leash sensor that tracks and records both pet-owner's and pet's length and time of physical activity.

13. A method for remotely monitoring the activities of at least one pet and at least one person within a health management system, the method comprising the steps of:
transmitting messages from at least one remote application, to a remote server;
configuring a pet device for:
  measuring physical activities of the pet, and sending information on physical activities of the pet to an interactive user communication device;
configuring an interactive user communication device for:
  receiving said messages from said remote server and
  measuring physical activities of the pet-owner and sending information on physical activities of the pet to the remote server;
configuring said remote application to communicate with the remote server for accessing the information on physical activities of the pet; and
transmitting messages to go to the interactive user communication device, wherein said pet device comprises a leash sensor that tracks and records both the pet-owner's and the pet's length and time of physical activity.

14. The method of claim 13 where the interactive user communication device also records various health-related parameters of the person.

15. The method of claim 13, wherein said remote server maintains a first database for storing information on various physical activities of the pet.

16. The method of claim 13, wherein said remote server maintains a second database for storing information on various physical activities of the pet owner.

17. The method of claim 13, wherein said pet device is formed within a pet collar.

18. The method of claim 13, wherein said interactive user communication device is a personal digital assistant (PDA) device.

19. The method of claim 13, wherein said interactive user communication device is a personal computer.

20. The method of claim 13, wherein said interactive user communication device is a mobile phone.

21. The method of claim 13, wherein said pet device detects the messages that are being received on the interactive user communication device through Bluetooth technology.

22. The method of claim 13, wherein said messages include medication and treatment reminders, for the pet and the pet owner.

23. The method of claim 13, wherein the remote application is a physician application.

24. The method of claim 13, wherein the remote application is a veterinarian application.

25. A method for remotely monitoring the activities of at least one pet and at least one person within a health management system, the method comprising the steps of:
transmitting messages from at least one remote application, to a remote server;
configuring a pet device for:
  measuring physical activities of the pet, and sending information on physical activities of the pet to an interactive user communication device;
configuring an interactive user communication device for:
  receiving said messages from said remote server and
  measuring physical activities of the pet-owner and sending information on physical activities of the pet to the remote server;

configuring said remote application to communicate with the remote server for accessing the information on physical activities of the pet; and transmitting messages to go to the interactive user communication device, where the interactive user communication device also records various health-related parameters of the person where one of the health-related parameters of the person is physical activity and the physical activity of the person is derived from the measurement of the physical activities of the pet.

\* \* \* \* \*